US010813860B2

(12) United States Patent
Buge et al.

(10) Patent No.: US 10,813,860 B2
(45) Date of Patent: *Oct. 27, 2020

(54) LEAVE-IN CHEMICAL FOAM COMPRISING BENZOYL PEROXIDE (71) Applicant: GALDERMA RESEARCH & DEVELOPMENT, Biot (FR)

(72) Inventors: Jean-Christophe Buge, Nice (FR); Karine Nadau-Fourcade, Villeneuve Loubet (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 142 days.

This patent is subject to a terminal disclaimer.

(21) Appl. No.: 15/129,549

(22) PCT Filed: Mar. 27, 2015

(86) PCT No.: PCT/EP2015/056785
§ 371 (c)(1),
(2) Date: Sep. 27, 2016

(87) PCT Pub. No.: WO2015/144907
PCT Pub. Date: Oct. 1, 2015

(65) Prior Publication Data
US 2017/0172877 A1 Jun. 22, 2017

Related U.S. Application Data (60) Provisional application No. 61/971,663, filed on Mar. 28, 2014.

(51) Int. Cl.
*A61K 8/38* (2006.01)
*A61Q 19/00* (2006.01)
*A61K 9/00* (2006.01)
*A61K 8/04* (2006.01)
*A61K 31/327* (2006.01)
*A61K 9/12* (2006.01)
*A61Q 19/08* (2006.01)
*A61K 47/02* (2006.01)
*A61K 47/12* (2006.01)

(52) U.S. Cl.
CPC .............. *A61K 8/38* (2013.01); *A61K 8/046* (2013.01); *A61K 9/0014* (2013.01); *A61K 9/12* (2013.01); *A61K 9/122* (2013.01); *A61K 31/327* (2013.01); *A61K 47/02* (2013.01); *A61K 47/12* (2013.01); *A61Q 19/00* (2013.01); *A61Q 19/08* (2013.01); *A61K 2800/22* (2013.01); *A61K 2800/882* (2013.01)

(58) Field of Classification Search
None
See application file for complete search history.

(56) References Cited

U.S. PATENT DOCUMENTS

| 5,952,372 | A | 9/1999 | McDaniel |
|---|---|---|---|
| 6,133,310 | A | 10/2000 | Parks |
| 6,177,092 | B1 | 1/2001 | Lentini et al. |
| 6,649,186 | B1 | 11/2003 | Robinson et al. |
| 2002/0061855 | A1 | 5/2002 | Parks |
| 2004/0184992 | A1 | 9/2004 | Abram |
| 2005/0123487 | A1 | 6/2005 | Spadini et al. |
| 2007/0237724 | A1 | 10/2007 | Abram et al. |
| 2009/0191248 | A1* | 7/2009 | Hoffman ............... A61K 8/43 424/402 |
| 2009/0214628 | A1* | 8/2009 | de Rijk ................. A01N 59/00 424/450 |
| 2010/0291160 | A1 | 11/2010 | Carver et al. |
| 2011/0008267 | A1 | 1/2011 | Arkin et al. |
| 2011/0236503 | A1* | 9/2011 | Kalli ................... A61K 31/327 424/616 |
| 2012/0114574 | A1 | 5/2012 | Touitou |
| 2013/0244976 | A1 | 9/2013 | Inamoto et al. |
| 2013/0317108 | A1 | 11/2013 | At |
| 2013/0338230 | A1 | 12/2013 | At |
| 2013/0338235 | A1 | 12/2013 | At |
| 2014/0364504 | A1 | 12/2014 | Uddin |
| 2015/0306124 | A1 | 10/2015 | Manetta et al. |
| 2017/0172877 | A1 | 6/2017 | Buge et al. |

(Continued)

FOREIGN PATENT DOCUMENTS

| CN | 104382863 A | 3/2015 |
|---|---|---|
| DE | 10 2008 029 357 A1 | 12/2009 |
| EP | 1 043 023 A1 | 10/2000 |

(Continued)

OTHER PUBLICATIONS

Anonymous. "Benzefoam Ultra", Drug Information Online—Drugs.com, Apr. 3, 2011, XP002739766. 9 pages.

(Continued)

*Primary Examiner* — David J Blanchard
*Assistant Examiner* — Sarah J Chickos
(74) *Attorney, Agent, or Firm* — Foley & Lardner LLP; Sunit Talapatra (57) ABSTRACT A composition is described that includes benzoyl peroxide. The composition can be formulated for a leave-in topical application and can be provided in the form of a leave-in foam intended to be applied to the skin. The composition can include:

at least one intermediate composition, at least one gas-generating agent, at least one agent that activates the gas-generating agent, and benzoyl peroxide.

A kit or a single multicompartment container including such a composition is also described.

36 Claims, 1 Drawing Sheet

(56) References Cited

U.S. PATENT DOCUMENTS

2017/0172972 A1    6/2017    Buge et al.

FOREIGN PATENT DOCUMENTS

| | | |
|---|---|---|
| EP | 1043023 A1 | 10/2000 |
| FR | 2761600 A1 | 10/1998 |
| FR | 2924944 A1 | 6/2009 |
| FR | 2943914 A1 | 10/2010 |
| JP | 2002-529391 A | 9/2002 |
| JP | 2004-217675 A | 8/2004 |
| WO | WO-00/27356 A1 | 5/2000 |
| WO | WO-2004/037225 A2 | 5/2004 |
| WO | WO-2005/058272 A1 | 6/2005 |
| WO | 20090069006 A2 | 6/2009 |
| WO | WO-2009/069006 A2 | 6/2009 |
| WO | WO-2012/001065 A2 | 1/2012 |
| WO | 20120085480 A1 | 6/2012 |
| WO | 20120085483 A1 | 6/2012 |
| WO | WO-2012/085480 A1 | 6/2012 |
| WO | WO-2012/085481 A1 | 6/2012 |
| WO | WO-2012/085483 A1 | 6/2012 |
| WO | WO-2014/201541 A1 | 12/2014 |
| WO | WO-2015/082659 A1 | 6/2015 |

OTHER PUBLICATIONS

Wikimedia Commons; "Citric Acid Speciation" https://commons.wikimedia.org/wiki/File:Citric_acid_speciation.png; accessed Jan. 10, 2020 (Year: 2011).

International Search Report corresponding to International Patent Application No. PCT/EP2015/056785, dated Jun. 5, 2015, with English translation, 6 pages.

\* cited by examiner

LEAVE-IN CHEMICAL FOAM COMPRISING BENZOYL PEROXIDE

CROSS-REFERENCE TO PRIOR APPLICATIONS

This application is a National Stage of PCT/EP2015/056785, filed Mar. 27, 2015, and designating the United States (published Pct. 1, 2015, as WO 2015/144907 A1), which claims priority under 35 U.S.C. § 119 to US Provisional Application No. 61/971,663, filed Mar. 28, 2014, hereby expressly incorporated by reference in its entirety and each assigned to the assignee hereof.

A subject matter of the present invention is a leave-in topical product in the form of a foam for the cosmetic and/or pharmaceutical treatment of the skin comprising dispersed benzoyl peroxide.

Despite all the progress obtained, the consumer is still on the lookout for compositions intended for a more practical and faster topical application. Foams make it possible to overcome problems of tolerance by better control of the dose, by virtue of their spreading properties and their low density.

In addition, some compounds used in compositions intended for a known topical application may result in side-effects which may limit the use and thus the effectiveness thereof. For example, some active principles exhibit the major disadvantage of inducing irritation which may result in mediocre tolerance of the product. This may thus create, on the part of the patient, behavior of nonobservance of the treatment and of dissatisfaction concerning said treatment.

There thus exists a need to develop novel pharmaceutical dosage forms which overcome the abovementioned disadvantages in terms of tolerance, effectiveness and observance.

First of all, the effectiveness of benzoyl peroxide (hereinafter also known as BPO) is related to its decomposition when it is brought into contact with the skin. This is because it is the oxidizing properties of the free radicals produced during this decomposition which result in the desired effect. Consequently, in order to keep the benzoyl peroxide at an optimum effectiveness, is important to prevent it from decomposing before use, that is to say during storage. In point of fact, benzoyl peroxide is an unstable chemical compound, which makes it difficult to formulate it in finished products. In addition, BPO exhibits a cross-reactivity with the other ingredients normally employed in topical formulations which either limits the use thereof or requires that other pharmaceutical dosage forms be found. Mention may be made, by way of example, of the reactivity of BPO in the presence of surfactants in emulsions, which limits the lifetime and the conditions of storage of products of this type.

Furthermore, BPO is particularly known to be tolerated with difficulty by consumers following an antiacne treatment. This tolerance with regard to BPO is highly variable depending on the formulation acting as vehicle for it. The patient is also often under the impression that, by applying a greater amount of product, curing will occur more rapidly. This behavior results in excessive irritation and in the treatment being stopped.

Thus, there therefore exists the need to have available novel pharmaceutical dosage forms and in particular forms of foam or foaming composition type which make possible better control of the dose and in which the benzoyl peroxide is stable, well tolerated, effective and pleasant to apply.

The composition according to the invention exhibits the advantage of being in the form of a foam which is generated at the time of use and which is very well tolerated. After its application, the composition according to the invention is not removed by rinsing.

One of the advantages of the composition of the invention is that of being particularly well tolerated, despite the fact that it is not removed by rinsing, as is shown by the examples illustrating one of the methods of evaluating the tolerance which are presented below. Various methods exist for evaluating the tolerance of a pharmaceutical or cosmetic product for cutaneous use, among which may be mentioned the in vivo "in used" or "human patch test" test but also the in vitro test, such as the test for measurement of the irritation on Reconstructed Human Epidermis (RHE) described in the OECD TG 439 protocol. The latter method is described in detail in example 3.

Foams or foaming compositions currently exist on the market. However, they all exhibit a certain number of disadvantages: Indeed there exists 3 types of foams or foaming compositions:

Aerosols, in which the foam is generated by a propellant gas but with the disadvantage of being aerosols exhibiting the well-known risks of the latter (contamination, breathing risks in particular).

Whipped creams, in which air bubbles are introduced into the product via a specific manufacturing process. This process exhibits the disadvantage of being restricting at the industrial level and requires a major capital cost with regard to the packaging equipment.

Foaming formulations which are low in foaming surfactants but are packaged in a packaging provided with a mechanical system which generates foam (pump with screen of Pulvorex type). This type of formulation exhibits the disadvantage of not being compatible with the use of active principles in the dispersed form, and requires the use of foaming surfactants which may induce irritation in leave-in products.

Thus, the need therefore remains to develop a cosmetic or pharmaceutical composition, the pharmaceutical dosage form of which is different from the known pharmaceutical dosage forms, in order to overcome their disadvantages and to make possible the use of BPO in the dispersed form in well-tolerated compositions intended for topical application to human beings, in particular leave-in compositions (that is to say that the composition is not removed by rinsing after it has been applied).

The aim of the present invention is thus to provide a composition which meets these needs.

The applicant has thus developed a novel cosmetic and/or pharmaceutical composition intended for a leave-in topical application which is provided in the form of a foam which advantageously does not comprise a foaming surfactant. Foaming surfactant are defined as surfactants which produce a voluminous, stable and creamy foam when they are mixed with water according to tests well-known to a person skilled in the art.

The following constitute foaming surfactants: anionic surfactants, cationic surfactants, amphoteric surfactants and nonionic surfactants of the family of the alkylpolyglucosides and glucamides.

The pharmaceutical dosage form according to the invention exhibits the advantage of guaranteeing good stability of the BPO. Furthermore, this formulation advantageously results in the production of a mild foam which is completely tolerated and non-irritating, which makes possible better coverage of the region to be treated and which makes it possible to overcome the problems of tolerance by better control of the dose, by virtue of the spreading properties and the low density of the foam.

Finally, advantageously, this pharmaceutical dosage form does not require, for the employment thereof, the use of propellant gases or aerosols. Thus, "aerosol" or "spray" foams are excluded from the scope of the invention. Likewise, the foams of the prior art of whipped cream type and/or foaming formulations requiring a mechanical foam-generating system (Pulvorex type) are also excluded from the invention.

Finally, a subject matter of the present invention is the cosmetic use of the composition according to the invention by topical application of this composition to the skin, and also a medicament intended for topical application to the skin comprising such a composition.

The present invention will be described in more detail in the description and examples below, and in the light of FIG. 1 appended to the present patent application.

The composition according to the invention is capable of taking the form of a foam due to its composition alone and can also be defined as a self-foaming composition for topical application.

A first subject matter of the present invention is consequently a composition comprising benzoyl peroxide intended for a leave-in topical application which is provided in the form of a foam, advantageously with a semisolid consistency, which advantageously does not comprise a foaming surfactant and which comprises a medium cosmetically or pharmaceutically compatible with a leave-in topical application, in particular to the skin and superficial body growths.

Composition which is provided in the form of a foam (also known below as self-foaming composition) is understood to mean a composition with a semisolid consistency having an aerated form comparable to a foam.

The composition according to the invention is a self-foaming composition which comprises at least the ingredients below:
- at least one intermediate composition or formulation,
- at least one gas-generating agent,
- at least one agent which activates the gas-generating agent, and
- benzoyl peroxide.

In a preferred aspect, the self-foaming composition comprises at least two intermediate compositions or formulations in variable proportions and in particular the ingredients below:
- at least one intermediate composition or formulation A,
- at least one intermediate composition or formulation B,
- at least one gas-generating agent,
- at least one agent which activates the gas-generating agent,
- benzoyl peroxide present in at least one of the intermediate compositions.

Preferably, the gas-generating agent is present in one of the abovementioned intermediate formulations.

In an even more preferred aspect, the self-foaming composition comprises at least two intermediate compositions or formulations in variable proportions and in particular the ingredients below:
- at least one intermediate composition or formulation A which comprises an agent which activates the gas-generating agent,
- at least one intermediate composition or formulation B which comprises the gas-generating agent,
- benzoyl peroxide present in at least one of said intermediate formulations A and B.

According to the invention, the composition is self-foaming, that is to say that it foams by simple mixing of the intermediate compositions A and B.

According to the invention, each intermediate composition (or formulation) can exhibit a viscosity (measured at 25° C. and at atmospheric pressure) of between 1 cP and 500 000 cP, advantageously between 500 cP and 350 000 cP, measured with a conventional method of Brookfield RV DV-II type: spindle 6, speed 2.

According to the invention, the gas generated by the gas-generating agent can be any physiologically compatible gas which makes it possible to obtain a foam, such as, for example, carbon dioxide ($CO_2$) or oxygen ($O_2$).

According to the invention, it being possible for the gas concentration to vary, the amount of bubbles in the composition can vary and can thus give a composition which can range from not very aerated to very strongly aerated.

According to the invention, agent which activates the gas-generating agent is understood to mean an ingredient which, by chemical reaction with the gas-generating agent, releases a gas. Preferably, an acid/base reaction is involved.

Thus, according to the invention, the self-foaming composition can preferably be provided in any form ranging from aerated to a highly expanded foam.

The composition according to the invention is suitable for topical application and can in addition comprise a physiologically acceptable medium, that is to say a medium compatible with the skin and superficial body growths. It is preferably a cosmetically or pharmaceutically acceptable medium.

In addition, the composition can comprise any active agent capable of exhibiting an optionally therapeutic activity. These active agents can, inter alia, be chosen from emollients, humectants, agents for combating free radicals, anti-inflammatory agents, vitamins, depigmenting agents, antiacne agents, antiseborrheic agents, antifungal agents, keratolytic agents, sunscreens, slimming agents or skin-coloring agents.

According to the invention, the self-foaming composition (that is to say, ready-to-be-applied composition) can have a pH of between 2 and 8, preferably between 3 and 7.

Insofar as the intermediate composition(s) (or formulation(s)) require storage in at least 2 compartments for reasons of stability of the ingredients, the present invention relates either to a single compartmentalized container (each compartment accommodating one intermediate formulation) preferably comprising 2 or 3 compartments or to a kit comprising each intermediate formulation stored independently from one another and physically separated.

The intimate mixing at the time of use (directly on the skin or on any other support) of the intermediate formulations makes it possible to obtain the self-foaming composition according to the invention.

More specifically, the intermediate composition (or formulation) A can be provided in the form of a solution, an emulsion (lotion, cream, emulsifier-free cream, milk, fluid cream) or a gel. This composition advantageously comprises the agent which activates the gas-generating agent, preferably an acid, in a sufficient amount (which can be provided in the form of an acid/base buffer at acidic pH), which can be, as nonlimiting example, the citric acid/sodium citrate pair.

The formulation B can be provided in the form of a solution, a gel or an emulsion (lotion, cream, emulsifier-free cream, milk, fluid cream). This composition advantageously comprises, in a sufficient amount, a gas-generating agent which can in particular be sodium bicarbonate.

Thus, another subject matter of the invention is a kit or a single multicompartment container as defined above, making possible the preparation at the time of use of a self-foaming composition according to the invention, separately comprising at least two intermediate formulations (or intermediate compositions):
an intermediate formulation A comprising at least one agent which activates the gas-generating agent; and
an intermediate formulation B comprising at least one gas-generating agent;
benzoyl peroxide being present in at least one of said intermediate formulations A and B.

Preferably, the benzoyl peroxide is present in the intermediate composition A.

Gas-Activating Agent:

The activating agent for the gas-generating agent (also denoted by "gas-activating agent") is a compound which reacts with the gas-generating agent by a chemical reaction (preferably an acid/base reaction) which releases a gas.

It is advantageously an acid, a partially salified polyacid salt or else a buffer solution of weak acid and of its conjugate base, or a mixture of such compounds.

According to the invention, the acid/base of said acid buffer can be any acid/base of the weak acid buffer, such as, for example, a citric acid/sodium citrate buffer or also a tartaric acid/sodium tartrate buffer. Mention will preferably be made of alpha-hydroxy acids, which are weak acids preferably having a pKa of between 2 and 6, such as citric acid, tartaric acid, malic acid or lactic acid but also phosphoric acid and pyrophosphoric acid and their partially salified salts, such as disodium pyrophosphate or sodium dihydrogenphosphate, also known as monosodium phosphate.

Preferably, according to the invention, the gas-activating agent is chosen from a tartaric acid/tartrate salt (for example sodium tartrate) buffer; a citric acid/sodium citrate buffer alone; phosphoric acid, monosodium phosphate, disodium pyrophosphate, which are alone or as a mixture with a citric acid/sodium citrate buffer.

According to a very preferred embodiment, the gas-activating agent is a citric acid/sodium citrate buffer, alone or as a mixture with monosodium phosphate and/or disodium pyrophosphate.

In compositions for sensitive skin or for damaged skin, such as skin suffering from acne, the content of citric acid/sodium citrate is preferably less than or equal to 2.4%, with respect to the total weight of the intermediate composition A, so as to limit any risk of tingling. In order to improve the tolerance and to avoid the sensation of tingling, preferably, the citric acid/sodium citrate buffer is employed as a mixture with disodium pyrophosphate or sodium dihydrogenphosphate.

According to the invention, said gas-activating agent can be present in the intermediate formulation A in an amount which can range from 0.001% to 95% by weight, with respect to the total weight of the intermediate formulation A.

Gas-Generating Agent:

Gas-generating agent is understood to mean any agent which has the property of generating a gas by a chemical reaction. Mention will be made, in this regard, of any compound which, when it is mixed with a weak acid, can form a gas by a chemical reaction equivalent to the following:

$$NaHCO_3 + RCOOH \rightarrow RCOONa + H_2O + CO_2$$

According to the invention, the gas which can be used in the formulation B can be carbon dioxide ($CO_2$).

According to the invention, the gas generated from the gas-generating agent present in the intermediate composition B is preferably carbon dioxide ($CO_2$).

According to the invention, the gas-generating agent is preferably chosen from sodium bicarbonate, potassium bicarbonate, sodium carbonate, potassium carbonate and their mixtures.

Preferably, according to the invention, the intermediate formulation B comprises an agent which generates carbon dioxide, which agent is particularly preferably sodium bicarbonate.

Said gas-generating agent can be present in the intermediate formulation B in an amount ranging from 1% to 10% by weight, preferably from 2% to 8% by weight, with respect to the weight of the formulation B.

According to the invention, the intermediate formulation A can exhibit an acidic pH, advantageously of between 1.0 and 6.0, and the intermediate formulation B can exhibit a basic pH, advantageously of between 7 and 12.

According to the invention, one (or the) intermediate formulation(s) A and B described above comprises benzoyl peroxide in an amount ranging from 0.0001% to 20% of benzoyl peroxide, preferably from 0.025% to 10%, more preferably still from 2.5% to 5%, by weight, with respect to the weight of the total composition.

In the present description, total composition or total formulation is understood to mean the composition of the product in the form of a foam after said intermediate compositions have been mixed. Preferably, the BPO is present in the intermediate composition A which exhibits a preferably acidic pH in order to optimize its stability.

The intermediate formulation A can be provided in all the pharmaceutical dosage forms compatible with the pharmaceutical dosage form desired for the final composition obtained by mixing the formulation A with the formulation B. Advantageously, the formulation A can be a gel, a solution, a suspension, an emulsion (cream, surfactant-free cream, lotion, milk, fluid cream), preferably a gel guaranteeing the suspension of the BPO. According to a particularly preferred embodiment, the intermediate formulation A is a gel.

The intermediate formulation B can be provided in all the pharmaceutical dosage forms compatible with the pharmaceutical dosage form desired for the final composition obtained by mixing the formulation B with the formulation A. Advantageously, the formulation B can be a gel, a solution, a suspension, an emulsion (cream, surfactant-free cream, lotion, milk, fluid cream), preferably an emulsion. According to a particularly preferred embodiment, the intermediate formulation B is an emulsion and comprises a fatty phase comprising one or more oils, as are described below.

Each intermediate formulation of the kit or of the multi-compartment container as defined above in accordance with the invention comprises a physiologically acceptable medium which conveys the compound or compounds and is chosen so that the compounds are capable of reacting with one another in order to form a self-foaming composition during the mixing of at least the intermediate formulations A and B.

Thus, the mixing at the time of use of at least two formulations, for example the formulation A and the formulation B, creates the self-foaming composition according to the invention. During the mixing of the two formulations A and B, the gas-generating agent, such as sodium bicarbonate, reacts with the gas-activating agent, such as the acid, and thus gives in particular the salt corresponding to the acid, water and $CO_2$ gas. It is this gas, trapped in the bubbles of the composition, which creates the foam which characterizes the self-foaming composition of the invention.

Thus, by the mixing of at least the intermediate formulation A and the intermediate formulation B, the foam composition, referred to as total composition, according to the invention is obtained.

Unreacted gas-activating agent and/or gas-generating agent may, of course, remain in the competition obtained after mixing at least the formulations A and B.

Advantageously, the kit or the single multicompartment container according to the invention can be designed so that, during the preparation of the composition according to the invention, the intermediate formulations A and B can be mixed in an A/B ratio by weight ranging from 0.5 to 2, preferably from 0.5 to 1.5, more preferably of approximately 1 (that is to say, from 0.9 to 1.1) and more preferably still of 1. This means that the kit can be designed in order to simultaneously release doses (by weight) of the intermediate compositions A and B which can be in a ratio by weight ranging from 2 doses of B per 1 dose of A to 2 doses of A per 1 dose of B, preferably from 2 doses of B per 1 dose of A to 3 doses of A per 2 doses of B. According to a preferred embodiment of the invention, the kit is designed in order to simultaneously release 1 dose by weight of A and 1 dose by weight of B.

According to the invention, the kit can be provided in any form compatible with, on the one hand, separate storage of the intermediate formulations A and B and, on the other hand, the ability to carry out the mixing of A and B at the time of use.

For example, the intermediate formulations A and B can be in a case with at least two separate compartments, each comprising A or B.

According to another aspect, the kit can be provided in the form of a syringe having at least two separate bodies, each provided with a piston, said two bodies comprising A and B and being designed in order to simultaneously release, by the exercise of a force on the piston, the desired doses of A and B.

The invention also relates to a process for the preparation of a composition according to the invention, characterized in that, in order to obtain the self-foaming composition, an intermediate formulation A and an intermediate formulation B of the kit as are defined above are mixed at the time of use in relative proportions by weight A/B which can range from 0.5 to 2, preferably from 0.5 to 1.5 and more preferably of 1.

In order to obtain an optimum foam (final composition), the inventors have searched experimentally for the optimum contents of gas-generating agent (preferably sodium bicarbonate) and of gas-activating agent (preferably citric acid and/or disodium pyrophosphate and/or sodium dihydrogenphosphate or monosodium phosphate).

Thus, it has been determined experimentally that, when the gas-activating agent is citric acid, the citric acid/sodium bicarbonate ratio is advantageously between 0.1 and 2, preferably between 0.5 and 1 and very preferably equal to 0.7.

In the same way, it has been determined that, when the gas-activating agent is disodium pyrophosphate, the disodium pyrophosphate/sodium bicarbonate ratio is between 0.5 and 5, preferably between 1 and 3 and very preferably is equal to 2.4.

In the same way, it has been determined that, when the gas-activating agent is sodium dihydrogenphosphate, the sodium dihydrogenphosphate monohydrate/sodium bicarbonate ratio is between 0.5 and 5, preferably between 1 and 3 and very preferably is equal to 2.

The sodium bicarbonate/citric acid, sodium bicarbonate/sodium pyrophosphate and sodium bicarbonate/sodium hydrogenphosphate ratios are exemplified in example 4.

Surprisingly, the combination formed of citric acid/sodium citrate, disodium pyrophosphate and a gelling system compatible with the pharmaceutical dosage form has made it possible to obtain a formulation with very stable physicochemical properties (see table I) and in which BPO is particularly stable (see table II), which does not generate any unpleasant sensation on the skin and which makes possible the release of gas and thus the creation of foam.

A composition is regarded as physically stable when its organoleptic characteristics, its pH, its viscosity and the homogeneity of the BPO do not change over time under different temperature conditions: ambient temperature (AT), 30° C. and 40° C.

According to the invention, ambient temperature corresponds to a temperature ranging from 15° C. to 25° C.

TABLE I

Physical stability of the intermediate formulation A5 (example 1) comprising BPO

| Formulation A5 | T0 | | T3 Months | T6 Months |
|---|---|---|---|---|
| pH | 3.54 | AT | 4.0 | — |
| | | 30° C. | 4.0 | — |
| | | 40° C. | 4.0 | — |
| Viscosity cP Brookfield RV DV-II | Spindle 3 speed 5 16000 | AT 30° C. 40° C. | Spindle 3 speed 5 17600 18200 21000 | Spindle 3 speed 2.5 33400 37500 37560 |

A composition is regarded as chemically stable when the content of active principle which it comprises does not change over time under different temperature conditions (AT, 30° C. and 40° C.).

According to the invention, the composition is regarded as stable when the content of BPO (expressed by weight with respect to the weight of the intermediate formulation) is included in the specifications ranging from 90% to 110%.

TABLE II

Chemical stability of the BPO in the intermediate formulation A5

| Formulation A5 | T0 | | T1 Month | T2 Months | T3 Months | T6 Months |
|---|---|---|---|---|---|---|
| % w/w BPO (HPLC) | 102 | AT 30° C. 40° C. | 102.6 103.4 | 101.1 103.8 | 104.7 101.8 99.3 | 101.6 99.0 93.6 |

The composition according to the invention can additionally comprise one or more agents chosen from dispersing agents, solubilizing agents, stabilizing agents, preservatives, fatty substances, thickening agents, dyes, fragrances, surfactants, gelling agents, complexing agents, neutralizing agents, non-foaming emulsifying agents, fillers, sequestering agents, reducing agents, odor maskers, plasticizing agents, softening agents, moisturizing agents, pigments, clays, inorganic fillers, inorganic colloids, polymers, proteins, pearlescent agents, waxes, oils, such as, for example, paraffins or silicones, fatty acids, solid esters of fatty alcohol or of fatty acids, gums or wetting agents.

Water-soluble dyes, such as FD&C Blue 1 (of empirical formula $C_{37}H_{34}N_2Na_2O_9S_3$), and fat-soluble dyes, such as Sudan Red III or Nile Red, exhibit the advantage of coloring one of the formulation intermediates. This coloring makes it possible to monitor the satisfactory mixing of the two formulation intermediates and to set off the formation of the foam. This coloring is presented in particular in the examples and in FIG. 1.

Gelling Agents for the Intermediate Formulation Comprising the Gas Activator

The intermediate composition A advantageously comprising at least one gas-activating agent preferably comprises at least one gelling agent and/or suspending agent.

Gels comprising BPO are known to be very complicated to stabilize. The viscosity and the suspending power of these formulations are often hard to guarantee over time. Furthermore, the formulation A can comprise large amounts of acid and electrolytes.

Mention may be made, as nonlimiting example of gelling agents and/or suspending agents which are resistant simultaneously to BPO, to electrolytes and to acidic pH values and which can participate in the compositions A according to the invention, of ready-for-use mixtures, such as Polyacrylate-13 & Polyisobutene & Polysorbate 20 sold by Seppic under the name Sepiplus 400®, polysaccharides with, as nonlimiting examples, xanthan gum, such as Xantural180® sold by Kelco, gellan gum sold under the name of Kelcogel® by Kelco, Sclerotium Gum sold under the name Amigel® by Alban Muller Industrie, guar gum and its derivatives, such as Hydroxypropyl Guar sold under the name Jaguar HP-105® by Rhodia, cellulose and its derivatives, such as microcrystalline cellulose and sodium carboxymethyl cellulose sold under the name Blanose CMC 7H4XF® by Hercules, hydroxypropylmethylcellulose, in particular the product sold under the name of Methocel E4M® Premium by Dow Chemical, or hydroxyethylcellulose, in particular the product sold under the name of Natrosol HHX 250® by Aqualon, the family of the aluminum magnesium silicates, such as Veegum K®, Veegum Plus® or Veegum Ultra® sold by Vanderbilt, the family of the modified starches, such as the modified potato starch sold under the name of Structure Solanace®, the family of the carrageenans, in particular divided into four large families: κ, λ, β and ω, such as the Viscarin® and Gelcarin® products sold by IMCD. Preferably, Vegum K® and Xantural 180® will be used in combination.

The gelling agent as described above can be used at the preferred concentrations ranging from 0.001% to 15% and more preferably ranging from 0.15% to 5% by weight, with respect to the weight of the intermediate formulation A.

Gelling Agents for the Intermediate Formulation Comprising the Gas Generator

Mention may be made, as nonlimiting example of gelling agents and/or suspending agents which are resistant both to electrolytes and to basic pH values and which can participate in the intermediate compositions B according to the invention, of acrylic acid polymers, such as Acrylates/C10-30 Alkyl Acrylate Crosspolymer, for example the carbomers described as insensitive to electrolytes sold under the name of Ultrez 20®, Ultrez 10@, Carbopol 1382®, Carbopol ETD2020NF® or Aqua SF1® sold by Lubrizol, the Ammonium Acrylate/Acrylamide Copolymer & Polyisobutene & Polysorbate 20 mixture sold by Seppic under the name Sepiplus 265®, polysaccharides with, as nonlimiting examples, xanthan gum, such as Xantural180® sold by Kelco, gellan gum sold under the name of Kelcogel® by Kelco, Sclerotium Gum sold under the name Amigel® by Alban Muller Industrie, guar gum and its derivatives, such as Hydroxypropyl Guar sold under the name Jaguar HP-105® by Rhodia, cellulose and its derivatives, such as microcrystalline cellulose and sodium carboxymethyl cellulose sold under the name Blanose CMC 7H4XF® by Hercules, hydroxypropylmethylcellulose, in particular the product sold under the name of Methocel E4M® Premium by Dow Chemical, or hydroxyethylcellulose, in particular the product sold under the name of Natrosol HHX 250® by Aqualon, the family of the aluminum magnesium silicates, such as Veegum K®, Veegum Plus® or Veegum Ultra® sold by Vanderbilt, the family of the modified starches, such as the modified potato starch sold under the name of Structure Solanace® or the tapioca flour starch known under the name of Naviance Tapioca P® sold by Akzo Novel, the family of the carrageenans, in particular divided into four large families: κ, λ, β and ω, such as the Viscarin® and Gelcarin® products sold by IMCD, or also a polyvinyl alcohol, also known under the abbreviation PVA, such as the product sold by Merck under the name POLYVINYL ALCOHOL 40-88®. Preferably, Vegum K® and Xantural 180® will be used in combination.

The gelling agent as described above can be used at the preferred concentrations ranging from 0.001% to 15% and more preferably ranging from 0.15% to 5% by weight, with respect to the weight of the intermediate formulation B.

Wetting Agents

The composition according to the invention can comprise one or more wetting agents. In this case, this or these wetting agents are present in the intermediate composition which comprises the BPO.

Among the wetting agents which have the role of reducing the surface tension and of allowing the BPO to be incorporated more easily in the formulation and mainly during the grinding thereof, use is preferably made, without this list being limiting, of a wetting agent which can preferably exhibit an HLB of 10 to 14, compounds of the family of the Poloxamers and/or of the glycols and more particularly Synperonic PE/L44® and/or Synperonic PE/L62® and/or compounds such as propylene glycol, dipropylene glycol, propylene glycol dipelargonate, lauroglycol or ethoxydiglycol. Preferably, the wetting agents are in the liquid form, so as to be easily incorporated in the composition without it being necessary to heat it. The wetting agent which is particularly preferred is Lutrol L44® sold by BASF®. It can be used at the preferred concentrations ranging from 0.001% to 5% and more preferably ranging from 0.01% to 1% by weight, with respect to the weight of the total formulation.

Humectants

Use is optionally made, among the humectants and/or emollients which have the role of moisturizing the skin and of facilitating the application of the formulation, without this list being limiting, of compounds such as a polyol which is miscible with water at ambient temperature (25° C.), in particular chosen from polyols having in particular from 2 to 20 carbon atoms, preferably having from 2 to 10 carbon atoms and preferably having from 2 to 6 carbon atoms, such as glycerol, glycol derivatives, such as propylene glycol, butylene glycol, pentylene glycol, hexylene glycol, dipropylene glycol, diethylene glycol and their mixtures, but also sugars (by way of example, glucose or lactose), polyethylene glycols (PEG) (by way of example, Lutrol E400®), urea or amino acids (by way of example, serine, citrulline, arginine, asparagine or alanine).

Mention may be made, as preferred humectant and/or emollient, of glycerol and propylene glycol.

The humectants can be used, alone or in combination, at preferred concentrations ranging from 0.001% to 30% and more preferably ranging from 0.01% to 10% by weight, with respect to the weight of the total formulation.

Chelating Agents

Mention may be made, among chelating agents, as non-limiting examples, of ethylenediaminetetraacetic acid (EDTA), diethylenetriaminepentaacetic acid (DTPA), ethylenediamindi(o-hydroxyphenylacetic acid) (EDDHA), (2-hydroxyethyl)ethylenediaminetriacetic acid (HEDTA), ethyldiaminedi(o-hydroxy-p-methylphenylacetic acid) (EDDHMA) and ethylenediaminedi(5-carboxy-2-hydroxyphenylacetic acid) (EDDCHA).

Mention may be made, as preferred chelating agent, of ethylenediaminetetraacetic acid (EDTA) sold in particular under the name Titriplex III®. It can be used at preferred concentrations ranging from 0.001% to 1% and more preferably from 0.05% to 0.1% by weight, with respect to the weight of the total formulation.

Cosmetic Active Principle

The composition according to the invention can comprise one or more cosmetic active principles, such as, for example, without implied limitation, allantoin with anti-irritant properties, antiacneic zinc gluconate, dipotassium glycyrrhizate for its anti-inflammatory properties or also healing alpha-bisabolol.

Fillers and Particles

Fillers and/or particles can be used to stabilize and boost the foam. Some of them have the specific property of being positioned at the water/air interface and of thus stabilizing this interface. Mention may be made, as fillers, of talc, metal oxides, such as zinc oxide or titanium dioxide $TiO_2$ T2000 sold by Merck under the name Eusolex® T-2000, clays, such as laponites, bentones or bentonites, but also cellulose ethers, such as Methocel® K100 LV sold by Dow, silicas, such as Aerosil® R972 sold by Evonik or Silica HDK® H13L sold by Wacker. They can be used at concentrations ranging from 0.01% to 10% by weight, with respect to the weight of the total formulation.

The Oils of the Fatty Phase

The composition according to the invention can also comprise a fatty phase.

This fatty phase can comprise, for example, vegetable, mineral, animal or synthetic waxes, oils or butters, silicone oils and their mixtures.

The fatty phase can, according to the pharmaceutical dosage form of the intermediate formulations, represent from 0% to 95% by weight, with respect to the weight of each intermediate formulation.

The fatty phase can be present in one and/or other of the intermediate compositions A and B. However, due to the instability of the BPO with regard to lipophilic molecules, when the composition according to the invention comprises a fatty phase, the latter is preferably present in the intermediate composition B.

The fatty phase of the composition according to the invention can comprise, for example, vegetable, mineral, animal or synthetic oils, silicone oils and their mixtures.

Mention may be made, as examples of mineral oil, for example, of liquid paraffins of different viscosities, such as Primol 352®, Marcol 82® and Marcol 152® sold by Esso.

Mention may be made, as vegetable oil, of sweet almond oil, palm oil, soybean oil, sesame oil, sunflower oil or olive oil.

Mention may be made, as animal oil or its substitute of vegetable origin, of lanolin, squalene or fish oil with, as derivative, the perhydrosqualene sold under the name Sophiderm® by Sophim.

Mention may be made, as synthetic oil, of an ester such as cetearyl isononanoate, such as the product sold under the name of Cetiol SN PH® by Cognis France, isononyl isononanoate, such as DUB ININ® sold by Stéarinerie Dubois, diisopropyl adipate, such as the product sold under the name of Crodamol DA® by Croda, isopropyl palmitate, such as the product sold under the name of Crodamol IPP® by Croda, or caprylic/capric triglyceride, such as Miglyol 812® sold by Univar. Mention may be made, as hydrogenated polyisobutene, of the Parleam® products sold by Rossow.

Mention may be made, as silicone oil, of a dimethicone, such as the product sold under the name of Q7-9120 Silicone Fluid®, with a viscosity of 20 cSt to 12 500 cSt, by Dow Corning, or of a cyclomethicone, such as the product sold under the name of ST-Cyclomethicone 5NF®, also by Dow Corning, or DC 9045 Elastomer Blend®, also by Dow Corning.

Nonionic Emulsifiers

The composition according to the invention and in particular the intermediate formulation B can also comprise solid fatty substances, such as natural or synthetic waxes, fatty acids, such as stearic acid, fatty alcohols, such as Speziol C18® Pharma or Speziol C16® sold by Cognis, and texturing agents of tribehenate type, such as Compritol 888® sold by Gattefossé, or hydrogenated castor oils, such as Cutina HR® sold by Cognis, or glyceryl stearate, such as Geleol® sold by Gattefossé. These nonliquid fatty substances can be used alone or as a mixture from 0 to 30% by weight, with respect to the weight of the total formulation. However, an exceptional foam quality has been observed when fatty alcohols of formula $CH_3(CH_2)_nOH$ (n is between 11 and 23) are present at contents of greater than 1% by weight, with respect to the weight of the total formulation.

Nonionic Emulsifiers

The composition according to the invention can also comprise nonionic emulsifiers. The latter are in particular present in the intermediate formulation or formulations which comprise a fatty phase (emulsions).

Mention may be made, as preferred emulsifiers, of hydrophilic emulsifiers such as Glyceryl Stearate (and) PEG-100 Stearate sold under the name Arlacel 165FL® by Uniquema, lipophilic emulsifiers such as Glucate SS® and Glucamate SSE®, Polyoxyethylene (21) Stearyl Ether sold under the name Brij 721® by Uniquema or also in the same family Brij S2® and Brij S20®, the self-emulsifying wax sold by Croda under the name of Polawax NF®. Mention may also made of nonionic surfactants exhibiting a high HLB, sorbitan esters, such as POE(20) sorbitan monooleate sold under the name of "Tween 80®" (HLB=15), POE(20) sorbitan monostearate sold under the name of "Tween 60®" (HLB=14.9), fatty alcohol ethers, such as POE (21) stearyl ether (HLB=15.5), or ceteareth-20 sold under the name of Eumulgin B2 PH® by Cognis (HLB of 15.5), or of nonionic surfactants with a low HLB, sorbitan esters, such as sorbitan monostearate (sold under the name of Span 60® by Uniquema), glycerol esters, such as glycerol monostearate (Cutina GMS® from Cognis), sucrose esters with a low HLB, such as sucrose distearate. In another form according to the invention, the surfactants which can be used are polyglycerol esters. They are esters of polyglycerolated fatty acids obtained by condensation of glycerol. Glycolipid emulsifiers, such as Montanov 202® sold by SEPPIC. Some emulsifiers can be sold in the form of a mixture, such as Emulium Kappa® and Emulium Delta® sold by Gattefossé. These surfactants can be used alone or in combination, so that the HLB of the system is greater than 12 and preferably greater than 15.

Such emulsifiers can be used in contents ranging from 0.01% to 30% by weight, with respect to the weight of the total composition, preferably from 0.1% to 15% and more preferably from 0.5% to 7%.

Preservatives

Mention may be made, as example of preservatives, of benzalkonium chloride, bronopol, chlorhexidine, chlorocresol and its derivatives, ethyl alcohol, phenoxyethanol, potassium sorbate, diazolidinyl urea, benzyl alcohol, parabens, sodium benzoate or their mixtures. Mention may be made, as preferred preservative system, of the phenoxyethanol and pentylene glycol combination.

The following examples illustrate the invention without restricting the scope thereof.

EXAMPLES

Example 1

Examples of Formulations

Examples of Formulations A: Intermediate compositions A comprising the gas-activating agent:

The intermediate formulations A were prepared according to the following process:
Stage 1: The gelling agents and then the activating agent or agents for the gas generator are added with stirring to the main water phase at a temperature of greater than 60° C.
Stage 2: At the same time, the grinding phase comprising the BPO, water, propylene glycol and Poloxamer 124 is carried out under high shear.
Stage 3: The mixture resulting from stage 2 is added to the main phase from stage 1 at a temperature of less than 30° C.
Stage 4: The additives, such as the dye Blue 1, pure or in solution, are added.

In the examples of formulations below, the amounts are expressed as percentage with respect to the weight of the intermediate formulation and not with respect to the weight of the total formulation (total formulation is understood to mean the mixture of the two intermediate formulations).

Example A1

| Ingredients | INCI Name | % |
| --- | --- | --- |
| WATER | WATER | q.s. for 100 |
| TITRIPLEX III ® | DISODIUM EDTA | 0.1 |
| VEEGUM K ® | MAGNESIUM ALUMINUM SILICATE | 2 |
| XANTURAL 180 ® | XANTHAN GUM | 0.7 |
| BLANOSE CMC 7H4XF PHARM ® | CELLULOSE GUM | 0.4 |
| CITRIC ACID MONOHYDRATE | CITRIC ACID | 3 |
| SODIUM CITRATE, TRISODIUM SALT | SODIUM CITRATE | 0.8 |
| LUTROL L44 ® | POLOXAMER 124 | 0.2 |
| PROPYLENE GLYCOL | PROPYLENE GLYCOL | 4 |
| BPO | BENZOYL PEROXIDE | 5.2 |

Example A2

| Ingredients | INCI Name | % |
| --- | --- | --- |
| WATER | WATER | q.s. for 100 |
| TITRIPLEX III ® | DISODIUM EDTA | 0.1 |
| AMIGEL GRANULE ® | SCLEROTIUM GUM | 1 |
| XANTURAL 180 ® | XANTHAN GUM | 0.3 |
| BLANOSE CMC 7H4XF PHARM ® | CELLULOSE GUM | 0.4 |
| CITRIC ACID MONOHYDRATE | CITRIC ACID | 3 |
| SODIUM CITRATE TRIHYDRATE | SODIUM CITRATE | 0.8 |
| LUTROL L44 ® | Poloxamer 124 | 0.2 |
| PROPYLENE GLYCOL | PROPYLENE GLYCOL | 4 |
| BPO | BENZOYL PEROXIDE | 5.2 |

Example A3

| Ingredients | INCI Name | % |
| --- | --- | --- |
| WATER | WATER | q.s. for 100 |
| SATIAXANE UCX 911 ® | XANTHAN GUM | 0.6 |
| VEEGUM K ® | MAGNESIUM ALUMINUM SILICATE | 2.5 |
| CITRIC ACID MONOHYDRATE | CITRIC ACID | 3.6 |
| SODIUM CITRATE, TRISODIUM SALT | SODIUM CITRATE | 2.6 |
| LUTROL L44 ® | POLOXAMER 124 | 0.2 |
| BPO | BENZOYL PEROXIDE | 10% |
| PROPYLENE GLYCOL | PROPYLENE GLYCOL | 4.0 |

Example A4

| Ingredients | INCI Name | % |
| --- | --- | --- |
| WATER | WATER | q.s. for 100 |
| SATIAXANE UCX 911 ® | XANTHAN GUM | 0.7 |
| VEEGUM K ® | MAGNESIUM ALUMINUM SILICATE | 2.5 |
| FD&C BLUE 1 | FD&C BLUE 1 | 0.0003 |
| DISODIUM PYROPHOSPHATE | DISODIUM PYROPHOSPHATE | 12 |

Example A5

| Ingredients | INCI Name | % |
|---|---|---|
| LUTROL L44 ® | POLOXAMER 124 | 0.2 |
| BPO | BENZOYL PEROXIDE | 5.2% |
| PROPYLENE GLYCOL | PROPYLENE GLYCOL | 4.0 |

Example A6

| Ingredients | INCI Name | % |
|---|---|---|
| WATER | WATER | q.s. for 100 |
| TITRIPLEX III ® | DISODIUM EDTA | 0.1 |
| SATIAXANE UCX 911 ® | XANTHAN GUM | 0.7 |
| VEEGUM K ® | MAGNESIUM ALUMINUM SILICATE | 2.5 |
| DISODIUM PYROPHOSPHATE | DISODIUM PYROPHOSPHATE | 6 |
| CITRIC ACID MONOHYDRATE | CITRIC ACID | 1.8 |
| SODIUM CITRATE, TRISODIUM SALT | SODIUM CITRATE | 1.3 |
| LUTROL L44 ® | Poloxamer 124 | 0.2 |
| BPO | BENZOYL PEROXIDE | 5.2% |
| PROPYLENE GLYCOL | PROPYLENE GLYCOL | 4.0 |

Example A7

| Ingredients | INCI Name | % |
|---|---|---|
| WATER | WATER | q.s. for 100 |
| TITRIPLEX III ® | DISODIUM EDTA | 0.1 |
| SATIAXANE UCX 911 ® | XANTHAN GUM | 0.7 |
| VEEGUM K ® | MAGNESIUM ALUMINUM SILICATE | 2.5 |
| DISODIUM PYROPHOSPHATE | DISODIUM PYROPHOSPHATE | 7.2 |
| CITRIC ACID MONOHYDRATE | CITRIC ACID | 1.4 |
| SODIUM CITRATE, TRISODIUM SALT | SODIUM CITRATE | 1 |
| LUTROL L44 ® | POLOXAMER 124 | 0.2 |
| BPO | BENZOYL PEROXIDE | 5.2% |
| PROPYLENE GLYCOL | PROPYLENE GLYCOL | 4.0 |
| FD&C BLUE 1 | FD&C BLUE 1 | 0.0005 |

| Ingredients | INCI Name | % |
|---|---|---|
| WATER | WATER | QSP 100 |
| TITRIPLEX III ® | DISODIUM EDTA | 0.1 |
| SATIAXANE UCX 911 ® | XANTHAN GUM | 0.7 |
| VEEGUM K ® | MAGNESIUM ALUMINUM SILICATE | 2.5 |
| PROBENZ SP ® | SODIUM BENZOATE | 0.2 |
| DISODIUM PYROPHOSPHATE | DISODIUM PYROPHOSPHATE | 7.2 |
| CITRIC ACID MONOHYDRATE | CITRIC ACID | 1.4 |
| SODIUM CITRATE TRISODIQUE | SODIUM CITRATE | 1 |
| LUTROL L44 ® | POLOXAMER 124 | 0.2 |
| BPO | BENZOYL PEROXIDE | 5.2% |
| PROPYLENE GLYCOL | PROPYLENE GLYCOL | 4.0 |

Example A8

| Ingredients | INCI Name | % |
|---|---|---|
| WATER | WATER | q.s. for 100 |
| TITRIPLEX III ® | DISODIUM EDTA | 0.1 |
| SATIAXANE UCX 911 ® | XANTHAN GUM | 0.7 |
| VEEGUM K ® | MAGNESIUM ALUMINUM SILICATE | 2.5 |
| PROBENZ SP ® | SODIUM BENZOATE | 0.2 |
| SODIUM DIHYDROGENPHOSPHATE | SODIUM PHOSPHATE | 6.2 |
| PHENOXETHOL ® | PHENOXYETHANOL | 0.5 |
| CITRIC ACID MONOHYDRATE | CITRIC ACID | 1.5 |
| SODIUM CITRATE, TRISODIUM SALT | SODIUM CITRATE | 0.5 |
| LUTROL L44 ® | POLOXAMER 124 | 0.2 |
| BPO | BENZOYL PEROXIDE | 5.2% |
| PROPYLENE GLYCOL | PROPYLENE GLYCOL | 4.0 |

Examples of Formulations B: Intermediate compositions B comprising the gas-generating agent:

The intermediate formulations B were prepared according to the following process:

Stage 1': The gelling agents are added with stirring to the main water phase at a temperature of greater than 60° C.

Stage 2': At the same time, the fatty phase (comprising the oils, waxes and surfactants) is heated to a temperature of greater than 60° C.

Stage 3': The emulsion is prepared by adding the fatty phase to the main phase resulting from stage 1' at a temperature of greater than 60° C.

Stage 4': The additives, such as the preservatives or ethanol, are added at a temperature appropriate for the additive.

Stage 5': The mixture is neutralized.

Stage 6': The sodium bicarbonate is added at a temperature of less than 40° C.

In the examples of formulations below, the amounts are expressed as percentage with respect to the weight of the intermediate formulation and not with respect to the weight of the total formulation.

Formulation B1

| Ingredients | INCI Name | % |
|---|---|---|
| WATER | WATER | q.s. for 100 |
| VEEGUM K ® | MAGNESIUM ALUMINUM SILICATE | 2.5 |
| SATIAXANE UCX 911 ® | XANTHAN GUM | 0.6 |
| TWEEN 80 ® | POLYSORBATE 80 | 0.8 |
| BRIJ S20 ® | STEARETH-20 | 2.8 |
| SPEZIOL C16-C18 ® | CETEARYL ALCOHOL | 1.5 |

-continued

| Ingredients | INCI Name | % |
|---|---|---|
| MARCOL 152 ® | MINERAL OIL | 8 |
| TRIETHANOLAMINE | TRIETHANOLAMINE | 1.2 |
| SODIUM BICARBONATE | SODIUM HYDROGENCARBONATE | 5 |

Formulations B2 and B3

| Ingredients | INCI Name | B2 (%) | B3 (%) |
|---|---|---|---|
| WATER | WATER | q.s. for 100 | q.s. for 100 |
| BLANOSE CMC 7H4XF ® | SODIUM CARBOXYMETHYLCELLULOSE | 0.5 | 0.2 |
| NATROSOL 200 HHX ® | HYDROXYETHYLCELLULOSE | 0.25 | 0.1 |
| BRIJ S20 ® | STEARETH-20 | 1.8 | 1.8 |
| ARLACEL 165 ® | GLYCERYL STEARATE (AND) PEG-100 STEARATE | 2.7 | 2.7 |
| SPEZIOL C16-C18 ® | CETEARYL ALCOHOL | 1 | 7 |
| PARLEAM ® | HYDROGENATED POLYISOBUTENE | 9 | 9 |
| TRIETHANOLAMINE | TRIETHANOLAMINE | 1.2 | 1.2 |
| PROPYLENE GLYCOL | PROPYLENE GLYCOL | 5 | 5 |
| PHENOXETOL | PHENOXYETHANOL | 1 | 1 |
| SODIUM BICARBONATE | SODIUM HYDROGENCARBONATE | 3 | 3 |

Formulation B4

| Ingredients | INCI Name | % |
|---|---|---|
| WATER | WATER | q.s. for 100 |
| VEEGUM K ® | MAGNESIUM ALUMINUM SILICATE | 3.5 |
| SATIAXANE UCX 911 ® | XANTHAN GUM | 1 |
| TWEEN 80 ® | POLYSORBATE 80 | 2 |
| STEARIC ACID | STEARIC ACID | 3 |
| SPEZIOL C16-C18 ® | CETEARYL ALCOHOL | 1.5 |
| PARLEAM ® | HYDROGENATED POLYISOBUTENE | 8 |
| TRIETHANOLAMINE | TRIETHANOLAMINE | 1.8 |
| SODIUM BICARBONATE | SODIUM HYDROGENCARBONATE | 3 |
| PHENOXETOL | PHENOXYETHANOL | 0.8 |

Formulation B5

| Ingredients | INCI Name | % |
|---|---|---|
| PURIFIED WATER | WATER | q.s. for 100 |
| VEEGUM K ® | MAGNESIUM ALUMINUM SILICATE | 2.5 |
| SATIAXANE UCX 911 ® | XANTHAN GUM | 0.5 |
| EUMULGIN B2 PH ® | CETEARETH-20 | 3 |
| SPEZIOL C16-C18 ® | CETEARYL ALCOHOL | 3 |
| COMPRITOL 888 PELLETS ® | GLYCERYL DIBEHENATE | 3 |
| MIGLYOL 812N ® | CAPRYLIC/CAPRIC TRIGLYCERIDE | 6 |
| NaOH 10% sol | SODIUM HYDROXIDE | 0.9 |
| PHENOXETHOL ® | PHENOXYETHANOL | 0.8 |
| SODIUM CARBONATE | SODIUM CARBONATE | 5 |

Formulation B6

| Ingredients | INCI Name | % |
|---|---|---|
| WATER | WATER | q.s. for 100 |
| VEEGUM K ® | MAGNESIUM ALUMINUM SILICATE | 2.5 |
| SATIAXANE UCX 911 ® | XANTHAN GUM | 0.6 |
| EUMULGIN B2 ® | CETEARETH-20 | 3 |
| MYGLYOL 812 ® | CAPRYLIC/CAPRIC TRIGLYCERIDE | 6 |
| SPEZIOL C16-C18 ® | CETEARYL ALCOHOL | 7 |
| TRIETHANOLAMINE | TRIETHANOLAMINE | 0.1 |
| SODIUM BICARBONATE | SODIUM HYDROGENCARBONATE | 5 |
| PHENOXYETHANOL | PHENOXYETHANOL | 0.8 |

Formulation B7

| Ingredients | INCI Name | % |
|---|---|---|
| PURIFIED WATER | WATER | q.s. for 100 |
| VEEGUM K ® | MAGNESIUM ALUMINUM SILICATE | 2.5 |
| SATIAXANE UCX 911 ® | XANTHAN GUM | 0.5 |
| EUMULGIN B2 PH ® | CETEARETH-20 | 3 |
| SPEZIOL C16-C18 ® | CETEARYL ALCOHOL | 3 |
| COMPRITOL 888 PELLETS ® | GLYCERYL DIBEHENATE | 3 |
| MIGLYOL 812N ® | CAPRYLIC/CAPRIC TRIGLYCERIDE | 6 |
| NaOH 10% sol | SODIUM HYDROXIDE | 0.9 |
| PHENOXETHOL ® | PHENOXYETHANOL | 0.8 |
| SODIUM BICARBONATE | SODIUM HYDROGENCARBONATE | 5 |

Formulation B8

| Ingredients | INCI Name | % |
|---|---|---|
| PURIFIED WATER | WATER | 63.3 |
| VEEGUM K ULTRA ® | MAGNESIUM ALUMINUM SILICATE | 2.5 |
| SATIAXANE UCX 911 ® | XANTHAN GUM | 0.5 |
| EUMULGIN B2 PH ® | CETEARETH-20 | 3 |
| SPEZIOL C6-C18 ® | CETEARYL ALCOHOL | 3 |
| COMPRITOL 888 PELLETS ® | GLYCERYL DIBEHENATE | 9 |
| MIGLYOL 812N ® | CAPRYLIC/CAPRIC TRIGLYCERIDE | 6 |
| NaOH 10% IN AQ. SOL. | SODIUM HYDROXIDE | 0.9 |
| PHENOXETHOL ® | PHENOXYETHANOL | 0.8 |
| SODIUM HYDROGENCARBONATE | SODIUM HYDROGENCARBONATE | 5 |
| EUDRAGIT RL100 ® | ACRYLATES/AMMONIUM METHACRYLATE COPOLYMER | 1 |
| ETHANOL RECTAPUR | ETHANOL | 5 |

The mixtures in a 1:1 ratio by weight of the intermediate compositions A and B described above are represented in the table below. A cross at the intersection of two formulation intermediates indicates that the mixture is possible and generates a foam with the desired properties.

| Formulation A | Formulation B | | | | | | | |
|---|---|---|---|---|---|---|---|---|
| | B1 | B2 | B3 | B4 | B5 | B6 | B7 | B8 |
| A1 | X | X | X | X | X | X | X | X |
| A2 | X | X | X | X | X | X | X | X |
| A3 | X | X | X | X | X | X | X | X |
| A4 | X | X | X | X | X | X | X | X |
| A5 | X | X | X | X | X | X | X | X |
| A6 | X | X | X | X | X | X | X | X |
| A7 | X | X | X | X | X | X | X | X |
| A8 | X | X | X | X | X | X | X | X |

Example 2

Measurements of Foam Density

Starting from the examples of formulations described in example 1, measurements of foam density were carried out at the time at which the 2 intermediate formulations A and B are brought into contact (T0) and then when the chemical reaction generated by bringing the two compositions into contact has finished:

Density formulation A5 (with blue dye)=1.108

Density formulation B7=1.021

Foam A5/B7 (50/50)=0.290

Figure 1:
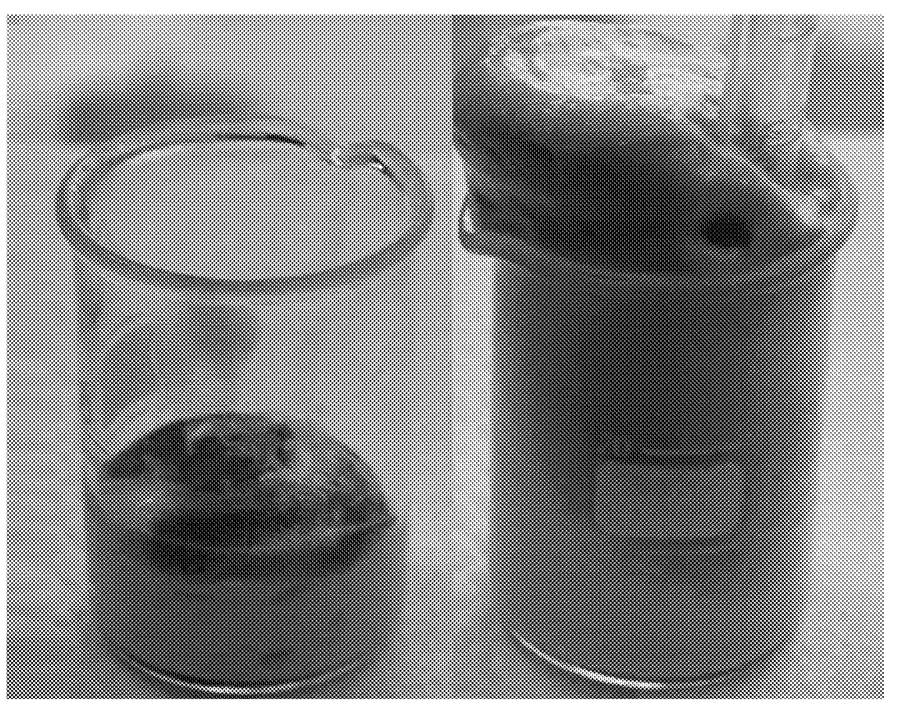
FIG. 1 shows photographs of a first composition in accordance with the invention obtained by mixing the two intermediate compositions A5 and B7 described in the examples, immediately after mixing these compositions and then when the reaction between these two compositions is complete (maximum volume of foam).

The measurement of the density of the foam shows that the volume has been increased by a factor of 4 and has been confirmed by the photographs in FIG. 1. The left-hand photograph represents the time of the mixing (T0) and the right-hand photograph represents the foam obtained when the acid/base chemical reaction is complete.

Example 3

Comparative Study of Measurement of the Irritation

Study Protocol.

The study is carried out according to the OECD TG 439 protocol in force for the short application time (contact time RHE/product 15 min). This protocol is appropriate for a long application time (contact time RHE/product 18 h).

The objective of this study is to evaluate the tolerance of the supports of the complete and intermediate formulations on reconstructed human epidermi (RHE, Episkin model) through:

the evaluation of the reduction of MTT (cell viability)

the measurement of the release of IL-1alpha (marker for irritation)

The formulations tested are:

An intermediate composition of acidic formulation: example A7 placebo (that is to say, not comprising BPO), An intermediate composition of basic formulation: example B7, The complete formulation composed of the mixture: A7 placebo+B7 (in a 50/50 ratio by weight), A commercial reference in the form of a cream.

Results of the Study:

| Mixture tested | Short exposure Viability (%) | Long exposure Viability (%) | Conclusion Irritant potential |
|---|---|---|---|
| B7 | 89.8 | 93.3 | Non-irritant |
| A7 placebo | 86.0 | 84.5 | Non-irritant |
| Complete formulation | 95.8 | 83.4 | Non-irritant |
| Commercial ref. | 99.8 | 91.1 | Non-irritant |

| Mixture tested | Short exposure IL-1alpha vs control | Long exposure IL-1alpha vs control |
|---|---|---|
| B7 | 1.5 | 2.0 |
| A7 placebo | 2.2 | 2.3 |
| Complete formulation | 1.9 | 3.1 |
| Commercial ref. | 2.4 | 3.6 |

The measurements of MTT according to the OECD protocol in force indicate that all the formulations tested are non-irritant.

The assaying of IL-1alpha of the complete formulation according to the invention after a short exposure time and a long exposure time shows a lower content of markers for irritation than after application of the commercial reference.

Example 4

The ideal content of citric acid, sodium pyrophosphate and sodium dihydrogenphosphate monohydrate for reacting with 5% of sodium bicarbonate has been established empirically. The values are expressed as percentage weight/weight with respect to the weight of each of the two intermediate formulations.

|                                      | Ratio1 | Ratio2 | Ratio3 |
|--------------------------------------|--------|--------|--------|
| Sodium bicarbonate                   | 5%     | 5%     | 5%     |
| Citric acid                          | 3.5%   | —      | —      |
| Disodium pyrophosphate               | —      | 12     | —      |
| Sodium dihydrogenphosphate monohydrate | —    | —      | 7.2%   |

In order for the pH of the formulation comprising the gas activator to exhibit an optimum compatibility with the skin, sodium citrate has been added in order to create a citric acid/sodium citrate buffer.

A portion of the citric acid/sodium citrate buffer can advantageously be replaced with disodium pyrophosphate and vice versa, like the contents cited by way of example in the table below:

TABLE III

The values are expressed as percentage weight/weight with respect to the weight of each of the two intermediate formulations.

|                        | E1   | E2   | E3   | E4  | E5   | E6    | E7   |
|------------------------|------|------|------|-----|------|-------|------|
| Sodium bicarbonate     | 5%   | 5%   | 5%   | 5%  | 3%   | 3%    | 3%   |
| Citric acid            | 3.5% | 1.75%| 1.4% | 0   | 2.1% | 1.05% | 0    |
| Sodium citrate         | 2.7% | 1.3% | 1%   | 0   | 1.6% | 1.15% | 0    |
| Disodium pyrophosphate | 0    | 6%   | 7.2% | 12% | 0    | 3.6%  | 7.2% |

A portion of the citric acid/sodium citrate buffer can advantageously be replaced with sodium dihydrogenphosphate monohydrate and vice versa, like the contents cited by way of example in table IV below:

TABLE IV

The values are expressed as percentage weight/weight with respect to the weight of each of the two intermediate formulations.

|                                        | E1   | E8   | E9  |
|----------------------------------------|------|------|-----|
| Sodium bicarbonate                     | 5%   | 5%   | 5%  |
| Citric acid                            | 3.5% | 1.5% | 0   |
| Sodium citrate                         | 2.7% | 0.5% | 0   |
| Sodium dihydrogenphosphate monohydrate | 0    | 6.2% | 10% |

In a specific form, it has been determined that, when the amount of citric acid is greater than or equal to 1.4%, the amount of foam is optimal when the disodium pyrophosphate is present in the composition according to the following equation:

$$[C] = 2.4[B] - 2.4[A]/0.7$$

when:
[C]=content by weight of disodium pyrophosphate in the intermediate composition A
[A]=content by weight of citric acid monohydrate in the intermediate composition A
[B]=content by weight of sodium bicarbonate in the intermediate composition B The equation above thus makes it possible to calculate the optimum contents between the sodium bicarbonate, the citric acid and the sodium pyrophosphate.

The invention claimed is:

1. A self-foaming composition formulated for a leave-on topical application, consisting of:
   (a) a gas-generating agent, present in an intermediate composition B, wherein the gas-generating agent is selected from the group consisting of sodium bicarbonate, potassium bicarbonate, sodium carbonate, potassium carbonate, and mixtures thereof;
   (b) an agent for activating the gas-generating agent, present in an intermediate composition A, wherein the agent for activating the gas-generating agent is selected from the group consisting of an acid, a partially salified polyacid salt, a buffer solution of weak acid and of its conjugate base, and mixtures thereof;
   (c) 0.025% to 10% benzoyl peroxide by weight, relative to the total weight of the composition, as an active principle, present in intermediate composition(s) A and/or B; and
   (d) one or more pharmaceutically acceptable excipients present in intermediate composition(s) A and/or B, selected from the group consisting of: (i) gelling agents; (ii) wetting agents; (iii) humectants; (iv) chelating agents; (v) active principles selected from the group consisting of allantoin, zinc gluconate, dipotassium glycyrrhizate, alpha-bisabolol, agents for combating free radicals, anti-inflammatory agents, vitamins, depigmenting agents, antiacne agents, antiseborrheic agents, antifungal agents, keratolytic agents, sunscreens, slimming agents and skin-coloring agents; (vi) fillers and particles; (vii) oils; (viii) nonliquid fatty substances; (ix) nonionic emulsifiers; (x) preservatives; (xi) dyes; (xii) dispersing agents; (xiii) solubilizing agents; (xiv) stabilizing agents; (xv) surfactants; (xvi) complexing agents; (xvii) neutralizing agents; (xviii) sequestering agents; (xix) reducing agents; (xx) plasticizing agents; (xxi) softening agents; (xxii) pigments; (xxiii) clays; (xxiv) inorganic colloids; (xv) proteins; (xvi) pearlescent agents; (xvii) waxes; (xviii) gums; and (xxix) water,
   wherein the self-foaming composition does not contain any foaming surfactants.

2. The self-foaming composition as defined by claim 1, wherein the benzoyl peroxide is present in composition A.

3. The self-foaming composition as defined by claim 1, wherein the gas generated from the gas-generating agent is carbon dioxide.

4. The self-foaming composition as defined by claim 1, wherein the gas-generating agent is present in composition B in an amount ranging from 1% to 10% by weight, with respect to the weight of composition B.

5. The self-foaming composition as defined by claim 1, wherein composition B has a pH between 7 and 12.

6. The self-foaming composition as defined by claim 1, wherein the agent that activates the gas-generating agent is selected from the group consisting of citric acid, tartaric acid, malic acid, lactic acid, phosphoric acid, pyrophosphoric acid, and the salts of these acids.

7. The self-foaming composition as defined by claim 6, wherein the agent that activates the gas-generating agent is a citric acid/sodium citrate buffer, alone or as a mixture with sodium phosphate and/or disodium pyrophosphate.

8. The self-foaming composition as defined by claim 1, wherein the agent activating the gas-generating agent is present in composition A in an amount ranging from 0.001% to 95% by weight, with respect to the total weight of composition A.

9. The self-foaming composition as defined by claim 1, wherein composition A exhibits an acidic pH.

10. The self-foaming composition as defined by claim 1, wherein composition A is provided in the form of a solution, a gel, or an emulsion.

11. The self-foaming composition as defined by claim 1, wherein composition B is provided in the form of a solution, a gel, or an emulsion.

12. The self-foaming composition as defined by claim 1, wherein the mixing of compositions A and B results in the formation of foam.

13. A medicament comprising the self-foaming composition as defined by claim 1, wherein the medicament is formulated for topical application to the skin.

14. A kit or single multicompartment container containing a self-foaming leave-on topical composition, the composition consisting of:
(a) a gas-generating agent, present in an intermediate composition B, wherein the gas-generating agent is selected from the group consisting of sodium bicarbonate, potassium bicarbonate, sodium carbonate, potassium carbonate, and mixtures thereof;
(b) an agent for activating the gas-generating agent, present in an intermediate composition A, wherein the agent for activating the gas-generating agent is selected from the group consisting of an acid, a partially salified polyacid salt, a buffer solution of a weak acid and of its conjugate base, and mixtures thereof;
(c) 0.025% to 10% benzoyl peroxide by weight, relative to the total weight of the composition, present in intermediate composition(s) A and/or B as an active principle; and
(d) one or more pharmaceutically acceptable excipients present in intermediate composition(s) A and/or B, selected from the group consisting of: (i) gelling agents; (ii) wetting agents; (iii) humectants; (iv) chelating agents; (v) active principles selected from the group consisting of allantoin, zinc gluconate, dipotassium glycyrrhizate, alpha-bisabolol, agents for combating free radicals, anti-inflammatory agents, vitamins, depigmenting agents, antiacne agents, antiseborrheic agents, antifungal agents, keratolytic agents, sunscreens, slimming agents and skin-coloring agents; (vi) fillers and particles; (vii) oils; (viii) nonliquid fatty substances; (ix) nonionic emulsifiers; (x) preservatives; (xi) dyes; (xii) dispersing agents; (xiii) solubilizing agents; (xiv) stabilizing agents; (xv) surfactants; (xvi) complexing agents; (xvii) neutralizing agents; (xviii) sequestering agents; (xix) reducing agents; (xx) plasticizing agents; (xxi) softening agents; (xxii) pigments; (xxiii) clays; (xxiv) inorganic colloids; (xv) proteins; (xvi) pearlescent agents; (xvii) waxes; (xviii) gums; and (xxix) water,
wherein compositions A and B do not contain any foaming surfactants;
the intermediate compositions A and B are separately contained; and
the mixing of compositions A and B results in the formation of foam.

15. The kit or single multicompartment container as defined by claim 14, wherein the kit or container is designed to simultaneously release doses of compositions A and B according to a ratio by weight ranging from 2 doses of B per 1 dose of A to 2 doses of A per 1 dose of B.

16. The kit or single multicompartment container as defined by claim 14, wherein the kit or container is designed for mixing compositions A and B in an AB ratio by weight ranging from 0.5 to 2.

17. A process for the preparation of a self-foaming composition, the process comprising:
(1) formulating the self-foaming composition as a leave-in topical composition consisting of:
(a) a gas-generating agent, present in an intermediate composition B, wherein the gas-generating agent is selected from the group consisting of sodium bicarbonate, potassium bicarbonate, sodium carbonate, potassium carbonate, and mixtures thereof;
(b) an agent for activating the gas-generating agent, present in an intermediate composition A, wherein the agent for activating the gas-generating agent is selected from the group consisting of an acid, a partially salified polyacid salt, a buffer solution of weak acid and of its conjugate base, and mixtures thereof;
(c) 0.025% to 10% benzoyl peroxide by weight, relative to the total weight of the composition, present in intermediate composition(s) A and/or B as an active principle; and
(d) one or more pharmaceutically acceptable excipients present in intermediate composition(s) A and/or B, selected from the group consisting of: (i) gelling agents; (ii) wetting agents; (iii) humectants; (iv) chelating agents; (v) active principles selected from the group consisting of allantoin, zinc gluconate, dipotassium glycyrrhizate, alpha-bisabolol, agents for combating free radicals, anti-inflammatory agents, vitamins, depigmenting agents, antiacne agents, antiseborrheic agents, antifungal agents, keratolytic agents, sunscreens, slimming agents and skin-coloring agents; (vi) fillers and particles; (vii) oils; (viii) nonliquid fatty substances; (ix) nonionic emulsifiers; (x) preservatives; (xi) dyes; (xii) dispersing agents; (xiii) solubilizing agents; (xiv) stabilizing agents; (xv) surfactants; (xvi) complexing agents; (xvii) neutralizing agents; (xviii) sequestering agents; (xix) reducing agents; (xx) plasticizing agents; (xxi) softening agents; (xxii) pigments; (xxiii) clays; (xxiv) inorganic colloids; (xv) proteins; (xvi) pearlescent agents; (xvii) waxes; (xviii) gums; and (xxix) water,
wherein compositions A and B do not contain any foaming surfactants; and
(2) mixing intermediate composition A with intermediate composition B in relative proportions by weight AB ranging from 0.5 to 2.

18. The self-foaming composition as defined by claim 1, wherein the gas-generating agent is sodium bicarbonate.

19. The self-foaming composition as defined by claim 4, wherein the gas-generating is present in composition B in an amount ranging from 2% to 8% by weight.

20. The self-foaming composition as defined by claim 5, wherein the pH is basic.

21. The self-foaming composition as defined by claim 6, wherein the agent that activates the gas-generating agent is selected from the group consisting of a citric acid/sodium citrate buffer alone; and phosphoric acid, sodium phosphate, and disodium pyrophosphate, alone or in a mixture with citric acid/sodium citrate buffer.

22. The self-foaming composition as defined by claim 9, wherein the acidic pH is from 1 to 6.

23. The self-foaming composition as defined by claim 10, wherein composition A is in the form of a gel.

24. The self-foaming composition as defined by claim 11, wherein composition B is in the form of an emulsion.

25. The self-foaming composition as defined by claim 1, wherein the oils are paraffins, silicones, fatty acids or solid esters of fatty alcohol or of fatty acids.

26. The self-foaming composition as defined by claim 15, wherein the ratio by weight of compositions A and B is from 2 doses of B per 1 dose of A to 3 doses of A per 2 doses of B.

27. The self-foaming composition as defined by claim 15, wherein the ratio by weight of compositions A and B is 1 dose of A per 1 dose of B.

28. The self-foaming composition as defined by claim 16, wherein the A/B ratio is from 0.5 to 1.5.

29. The self-foaming composition as defined by claim 16, wherein the A/B ratio is from 0.9 to 1.1.

30. The self-foaming composition as defined by claim 16, wherein the A/B ratio is 1.

31. The process as defined by claim 17, wherein the ratio of A/B is from 0.5 to 1.5.

32. The process as defined by claim 17, wherein the A/B ratio is 1.

33. The self-foaming composition as defined by claim 1, wherein compositions A and/or B comprise 0.025% to 5% benzoyl peroxide by weight, relative to the total weight of the composition, as an active principle.

34. The self-foaming composition as defined by claim 1, wherein compositions A and/or B comprise 2.5% to 10% benzoyl peroxide by weight, relative to the total weight of the composition, as an active principle.

35. The self-foaming composition of claim 1, wherein the gelling agents are selected from the group consisting of polysaccharides, the family of aluminum magnesium silicates, modified starches, carrageenans, acrylic acid polymers, polyacrylate-13 & polyisobutene & polysorbate 20 mixtures, ammonium acrylate/acrylamide & polyisobutene & polysorbate 20 mixtures, and polyvinyl alcohols.

36. The self-foaming composition of claim 35, wherein the polysaccharides are selected from the group consisting of xanthan gum, gellan gum, sclerotium gum, guar gum and its derivatives, cellulose and its derivatives, and combinations thereof.

\* \* \* \* \*